United States Patent [19]
Kohno

[11] Patent Number: 5,162,867
[45] Date of Patent: Nov. 10, 1992

[54] SURFACE CONDITION INSPECTION METHOD AND APPARATUS USING IMAGE TRANSFER

[75] Inventor: Michio Kohno, Tokyo, Japan
[73] Assignee: Canon Kabushiki Kaisha, Tokyo, Japan
[21] Appl. No.: 645,563
[22] Filed: Jan. 24, 1991
[30] Foreign Application Priority Data
   Jan. 26, 1990 [JP] Japan .................................. 2-015109
   May 2, 1990 [JP] Japan .................................. 2-115215
[51] Int. Cl.⁵ .......................................... G01N 21/88
[52] U.S. Cl. ..................................... 356/237; 356/394
[58] Field of Search ................................. 356/237, 394

[56] References Cited
U.S. PATENT DOCUMENTS
  4,330,775  5/1982  Iwamoto et al. .............. 356/237 X
  4,586,822  5/1986  Tanimoto .......................... 356/394
  4,718,767  1/1988  Hazama .......................... 356/394 X
  4,758,094  7/1988  Wihl et al. ......................... 356/394
  4,875,076  10/1989 Torigoe et al. .................... 355/30 X Primary Examiner—Vincent P. McGraw
Attorney, Agent, or Firm—Fitzpatrick, Cella, Harper & Scinto

[57] ABSTRACT

An optical unit for inspecting the state of latent images or photochromic images on a wafer is mounted on an exposure apparatus. Before actually printing images on a product wafer, a reticle pattern is printed on the wafer using a wafer on which a resist for development is coated or a photochromic film for forming photochromic images is formed. Latent images or photochromic images of the reticle pattern thus obtained are inspected by the inspection unit. According to the result of inspection, it is determined whether or not any foreign particle of a level that would affect printing is present on the reticle.

24 Claims, 19 Drawing Sheets

FIG. 16(A)
FIG. 16(B)
FIG. 16(C)
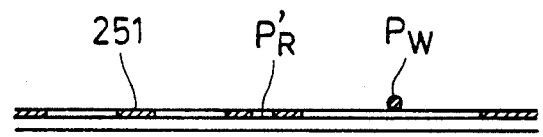
FIG. 16(D) $S_A$
FIG. 16(E) $S_C$
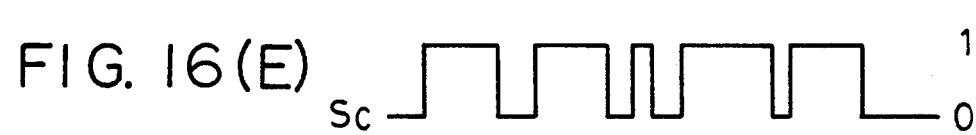
FIG. 16(F)
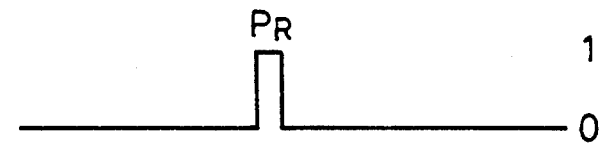

SURFACE CONDITION INSPECTION METHOD AND APPARATUS USING IMAGE TRANSFER

BACKGROUND OF THE INVENTION

1. Field of the Invention

This invention relates to a surface state inspection apparatus, and more particularly, to a surface state inspection apparatus which is suitable when detecting foreign particles, such as opaque dust particles or the like, other than a circuit pattern, adhered to a substrate, such as a reticle, a photomask or the like, in the semiconductor production process using a light exposure method.

2. Description of the Prior Art

In the IC (integrated circuit) production process, in general, an IC is produced by transferring a circuit pattern for exposure formed on a substrate, such as a reticle, a photomask or the like, to the surface of a wafer coated with a resist using a semiconductor printing apparatus (a stepper or a mask aligner).

At this time, if foreign particles, such as dust particles or the like, are present on the surface of the substrate, the foreign particles are also transferred in the transfer operation, causing a decrease in the yield of the IC production.

Particularly when a circuit pattern is repeatedly printed on the surface of a wafer by a step-and-repeat method using a reticle, one foreign particle on the surface of the reticle is printed on the entire surface of the wafer, causing a large decrease in the yield of the IC production.

Accordingly, it is indispensable to inspect for the presence of foreign particles on a substrate in the IC production process, and various kinds of inspection methods have been proposed. For example, FIG. 1 illustrates a method which utilizes the property of a foreign particle to isotropically scatter light. In FIG. 1, after being reflected by a mirror 511, for scanning and passing through a lens 512, a light beam from a laser 510 is directed upwardly or downwardly by interposing or withdrawing a mirror 513, and is incident upon the upper surface and the back surface of a substrate 515 reflected by two mirrors 514 and 545, respectively. The light beam scans the surfaces of the substrate 515 by rotating or vibrating the mirror 511 for scanning. A plurality of photosensing units 516, 517 and 518 are provided at positions separated from the optical paths of directly reflected light and transmitted light from the substrate 515. The presence of a foreign particle on the substrate 515 is detected using output signals from the plurality of photosensing units 516, 517 and 518.

That is, since diffracted light from a circuit pattern has a strong directional significance, output values from the respective photosensors are different from one another. If a light beam is incident upon a foreign particle, the incident light beam is isotropically scattered. As a result, output values from the plurality of photosensors become equal. Accordingly, by comparing the output values at this time, the presence of the foreign particle is detected.

FIG. 2 illustrates a method which utilizes the property of a foreign particle to disturb the polarizing characteristic of an incident light beam. In FIG. 2, the light beam from the laser 510 is made to have a predetermined polarization state via a polarizer 519, the mirror 511 for scanning and the lens 512, is directed upwardly or downwardly by interposing or withdrawing the mirror 513, and is incident upon the upper surface and the back surface of the substrate 515 by being reflected by the two mirrors 514 and 545, respectively. The light beam scans the substrate 515 with the mirror 511. Two photosensing units 521 and 523 having polarizers 520 an 522 in front thereof are provided at positions separated from the optical paths of directly reflected light and transmitted light from the substrate 515. A difference in the amount of received light due to a difference in the polarization rate between diffracted light from a circuit pattern and scattered light from a foreign particle is detected by the two photosensing units 521 and 523. The circuit pattern and the foreign particle on the substrate 515 are thereby discriminated.

However, the conventional methods have the following common disadvantages: That is, since inspection is performed by directly detecting light from an illuminated reticle by detectors, it is difficult to detect how a defect actually causing a problem in printing adversely influences a printed pattern. In the conventional methods, for example, a defect actually causing a problem in printing and a defect hardly influencing a printed pattern, that is, a defect which need not be detected, may be detected without being discrimated.

SUMMARY OF THE INVENTION

The present invention has been made in consideration of the above-described problems in the prior art.

It is an object of the present invention to provide an inspection method and apparatus which can detect foreign particles and the like in a short time while avoiding inefficiency that the presence of the foreign particles and the like is confirmed only after printing and developing a pattern, and wherein foreign particles and the like actually causing a problem in printing can be securely detected, reliability in the determination of the presence of foreign particles having an adverse influence during actual exposure operation is increased, and the state of the adverse influence can be easily detected.

It is another object of the present invention to provide an inspection method and apparatus wherein dust adhered to an original, such as a reticle or the like, and adversely influencing exposure is detected and discriminated from dust directly adhered to a transfer material for inspection, such as a water or the like.

The invention is directed to a method for inspecting the surface state of an original having a pattern thereon in which the original is illuminated to transfer images of the pattern to a transfer member. The images transferred to the transfer member are inspected to determine the surface state of the original without development processing.

These and other objects and features of the present invention will become more apparent from the following detailed description of the preferred embodiments.

BRIEF DESCRIPTION OF THE DRAWINGS

FIGS. 16(A)–16(F) illustrate a reticle, its photochromic image pattern, and signals obtained therefrom;

DESCRIPTION OF THE PREFERRED EMBODIMENTS

Figure 1:
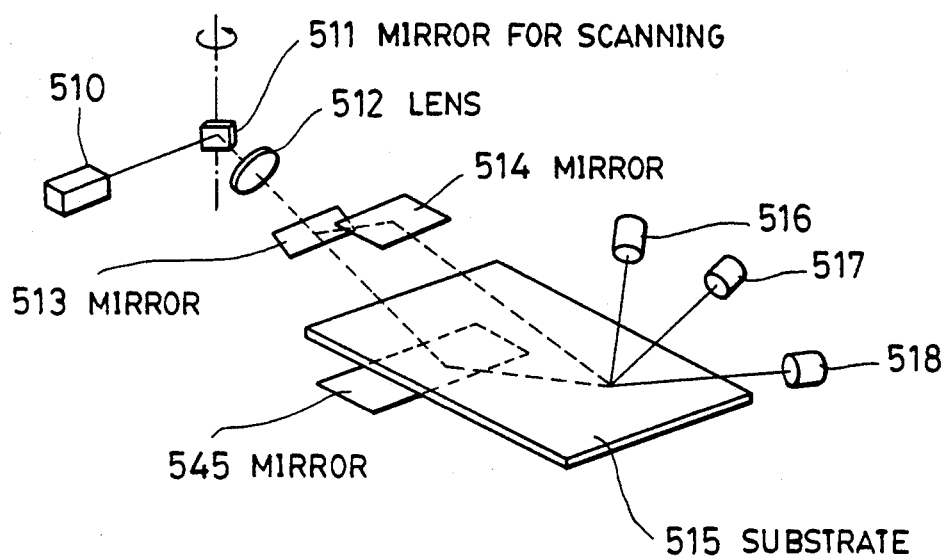
FIGS. 1 and 2 are drawings illustrating conventional examples.
Figure 2:
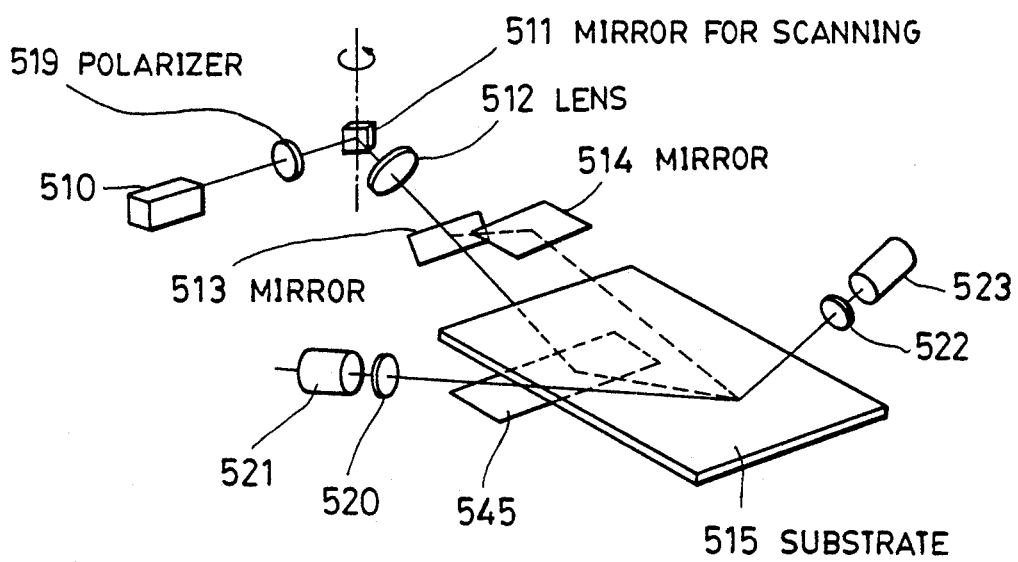
Figure 3:
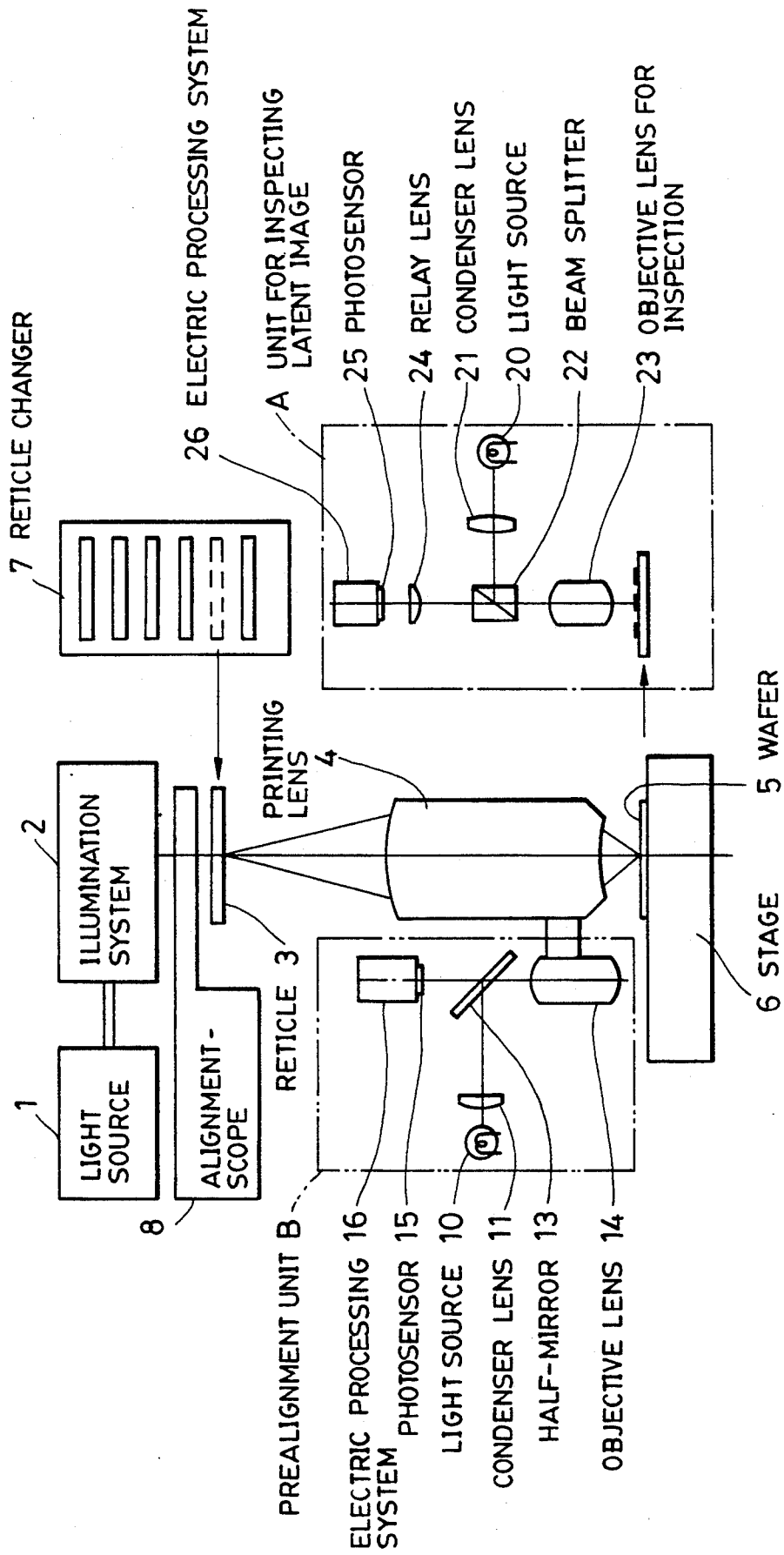
FIG. 3 illustrates the configuration of a first embodiment of the present invention.

FIG. 3 illustrates the configuration of a first embodiment of the present invention.

In FIG. 3, a light source 1 for printing (exposure) comprises an extra-high-pressure mercury-vapor lamp, an excimer laser or the like.

An illumination system 2 uniformly illuminates nearly the entire surface of a reticle 3 with a light beam issued from the light source with a predetermined aperture angle. The reticle 3 is fed from a reticle changer 7 onto an object surface (an exposure stage) of a printing lens 4.

A circuit pattern on the reticle 3 is subjected to reduced transfer on a wafer 5 by the printing lens 4. A resist for forming a latent image is coated on the wafer 5. In the present embodiment, the pattern on the reticle 3 is transferred and exposed on the wafer 5 at least once. Subsequently, the wafer 5 is fed to a unit A for inspecting latent images by moving a stage 6.

Next, the unit A for inspecting latent images will be explained.

A light source 20 for inspection emits a light beam having a wavelength within the wavelength region wherein a latent image on a wafer can be observed and the latent image is not erased. A laser, a halogen lamp (having a color filter) or the like may be used as the light source 20. The optical system of the unit A illuminates a latent-image region (a transfer region of the reticle pattern) on the wafer 5 via a condenser lens 21, a beam splitter 22, and an objective lens 23 for inspection. The reflected light returns via the objective lens 23 and the beam splitter 22, and is condensed onto a photosensor 25 by a relay lens 24. The surface of the wafer 5 and the surface of the photosensor 25 are set in an optically conjugate relationship. The photosensor 25 is a light-position sensor, such as a two-dimensional CCD array or a pickup tube. According to the above-described system configuration, the circuit pattern on the reticle 3 including foreign particles is first transferred to the wafer 5, and is then imaged on the surface of the photosensor 25 of the inspection unit A.

Figure 4:
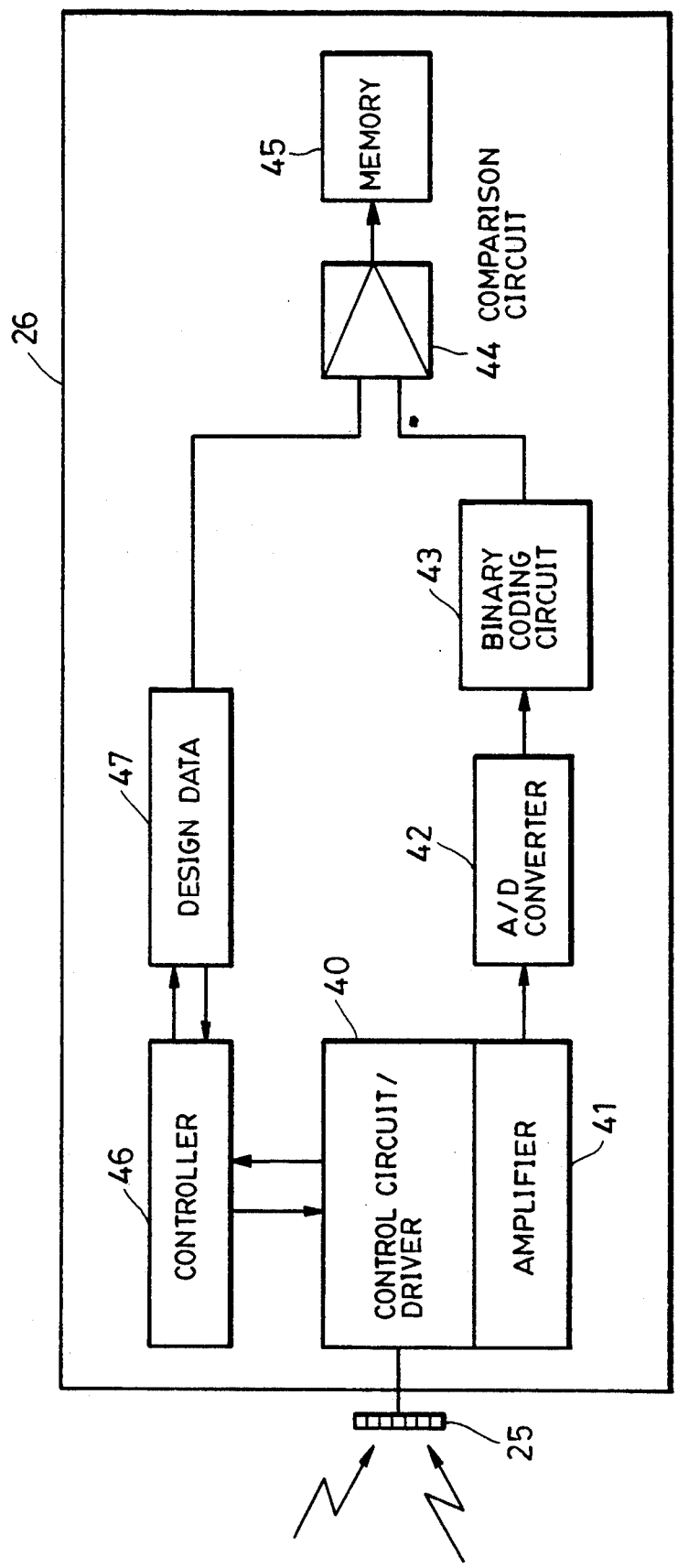
FIG. 4 is the circuit diagram of an electric processing system shown in the FIG. 3 embodiment.

The output from the photosensor 25 is processed by an electric processing system 26 to detect foreign particles. FIG. 4 illustrates a circuit of the electric processing system 26.

An output from the light-position sensor (photosensor) 25 is received in a control circuit/driver 40 whose timing is controlled by a controller 46 for commanding the setting of inspection conditions, for example, the start and end of positioning inspection of a wafer. The received signal is amplified by an amplifier 41. The amplified signal is subjected to A/D conversion by an A/D converter 42, and is then subjected to binary coding by a binary coding circuit 43. The controller 46 reads design data of the reticle pattern previously stored in a memory 47 within the apparatus, and the binary coded data are compared with the design data by a comparison circuit 44. If the two output data do not coincide, the controller 46 determines that a foreign particle is present on the reticle 3, and stores its position, size and the like within a memory 45.

In FIG. 3, there is shown an alignment unit B for positioning a wafer and setting it to an exposure position feeding it by a predetermined amount. There are two methods in gross for finally positioning a wafer relative to a reticle.

One is a TTL (through-the lens) method wherein alignment is performed using an alignmentscope 8 with the aid of the printing lens 4. In this method, the unit B performs the function of the prealignment of a wafer.

Another is an off-axis method wherein positioning of a wafer is completed outside the exposure position, and the wafer is then fed in that state for exposure by increasing the feed accuracy of the stage 6. In this method, the unit B performs the function of the final alignment of the wafer.

In any method, the basic configuration of the alignment unit B consists of a light source 10, an objective lens 14, a photosensor 15 and an electric processing system 16 (although a condenser lens 11, a half-mirror 13 and the like are also used), as shown in FIG. 3. The detail of this unit is disclosed, for example, in U.S. Pat. No. 4,794,648. Accordingly, in consideration of the configuration of the entire stepper, the alignment unit B may have the function of the unit A for inspecting latent images. That is, the configuration of an electric processing system 26 shown in FIG. 4 may be added to the electric processing unit 16, and the above-described inspection of the latent image may be performed with returning the wafer 5 to the unit B when inspecting the latent image.

As described above, in the present apparatus, the optical unit for inspecting the state of a latent image on a wafer is mounted on the exposure apparatus. Before actually printing a product wafer, a reticle pattern is printed on a wafer coated with a resist on which a latent image is formed. The latent image of the reticle pattern thus obtained is inspected by the above-described inspection unit. According to the result of inspection, the apparatus determines whether or not any foreign particle of a level influencing printing is present on the reticle. Also by illuminating a substrate, such as a reticle or the like, with light having the same wavelength as that of exposing light, and inspecting the pattern on the substrate by receiving light from the substrate (on the resist), the present embodiment has the effect that the apparatus can determine whether or not any foreign particle of a level actually influencing printing is present.

Figure 5:
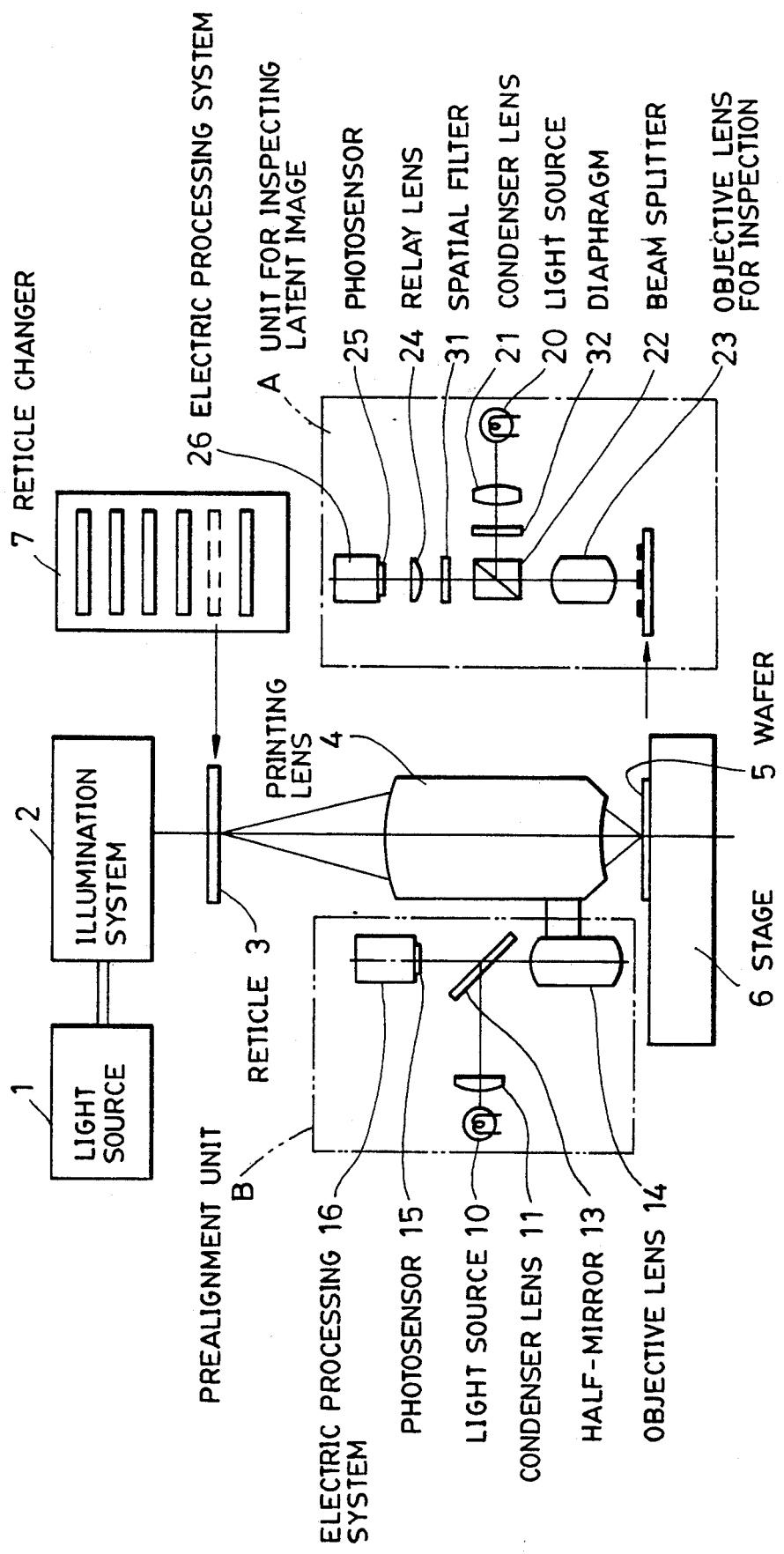
FIG. 5 illustrates the configuration of a second embodiment of the present invention.

An embodiment different from the foregoing embodiment is shown in FIG. 5. One of different points from the FIG. 3 embodiment is the use of a spatial filter within the inspection unit. An explanation will now be provided of advantages when the spatial filter 31 is inserted.

Figure 6A:
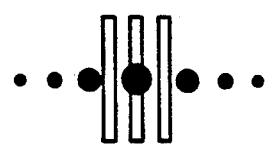
FIGS. 6(a) and 6(b) illustrate circuit patterns and diffracted light therefrom.
Figure 6B:
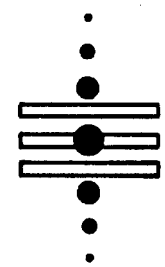
Figure 7A:
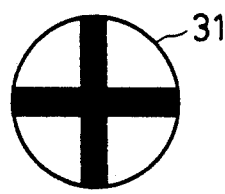
FIGS. 7(a) through 7(d) illustrate various examples of spatial filters.

In general, a (latent image) circuit pattern on a wafer has lines in the vertical and horizontal directions. When a laser beam is projected on these lines, diffracted light is distributed in directions perpendicular to the pattern, as shown in FIGS. 6(a) and 6(b). Accordingly, if a spatial filter (FIG. 7(a)) to cut such diffracted light is provided at the position of the exit of an objective lens 23 (FIG. 5) for inspection, lines in the vertical and horizontal directions are not imaged on the reimaging surface (photosensitive surface) of the photosensor 25. To the contrary, scattered light from a foreign particle passes through the spatial filter and is reimaged since the shape of the foreign particle is close to a circle.

According to the above-described function, only the foreign particle can be electrically detected in a state wherein the circuit pattern on the wafer is cancelled. Accordingly, in the FIG. 4 circuit, the circuitry for comparing data obtained from a wafer with design data becomes unnecessary, and the output from the binary coding circuit 43 can be directly sent to the memory 45. Hence, the configuration of the electric system is greatly simplified.

Figure 7B:
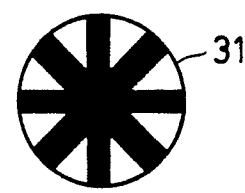

FIG. 7(b) is a spatial filter for optically cancelling lines in oblique 45° directions as well as in the vertical and horizontal directions on a circuit pattern. This filter is disposed at the position of the exit of the lens 23 in the same manner as the filter shown in FIG. 7(a).

The apparatus has the possibility that, actually, foreign particles adhered to the wafer after exposure are also detected together with the latent images of foreign particles transferred from the reticle. In order discriminate between the two kinds of foreign paticles, the reticle pattern is repeatedly exposed and transferred to the wafer two times (steps), and the above-described inspection is performed for respective two chips. The apparatus may check whether or not a foreign particle is detected on the same position on the two chips. For a foreign particle adhered to the reticle, the foreign particle must be detected at the same position on all exposed chips. To the contrary, for a foreign paticle adhered to the wafer, there is little probability that a foreign particle having the same size adheres to the same position on adjacent chips.

Figure 7C:
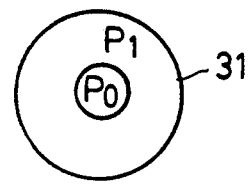

FIG. 7(c) shows a third example of the spatial filter 31 to be disposed at the position of the exit pupil of the objective lens 23. This filter comprises a phase plate used in a phase contrast microscope system.

While its circumferential portion $P_1$ comprises a mere plane parallel plate, an optical thin film is deposited in vacuum on its central portion $P_0$ in order to provide a phase difference of $\pi/2$ with respect to the circumferential portion $P_1$. By using such a phase plate, a phase difference between an exposed portion and an unexposed portion of a latent image can be detected as an intensity difference on the photosensitive surface with a high contrast.

Figure 7D:
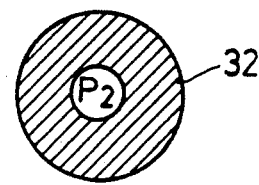

In order to enhance the effect of such phase difference detection method, a laser is used as the light source 20 in the light projection unit. A diaphragm 32 as shown in FIG. 7(d) is provided at the position of the exit of the objective lens 23 on the incident optical path toward the beam splitter 22, in the same manner as the spatial filter 31. The diaphragm 32 is open at its central portion ($P_2$). The size of the opening is equal to the size of the central portion ($P_0$) of the above-described spatial filter 31 in the arrangement shown in FIG. 5. The reason is as follows:

In general, since the diaphragm 32 and the spatial filter 31 are in an optically imaging relationship with each other, a light beam issued from a point on the diaphragm 32 passing through the beam splitter 22 and the objective lens 23 is reflected by the latent-image surface, returns through the objective lens 23 and the beam splitter 22, and is imaged on a corresponding point in the central portion of the spatial filter 31. This light beam is termed a 0-order light in the phase difference method. In order to obtain a high contrast, it is necessary to provide the 0-order light with a strict phase difference.

Figure 8:
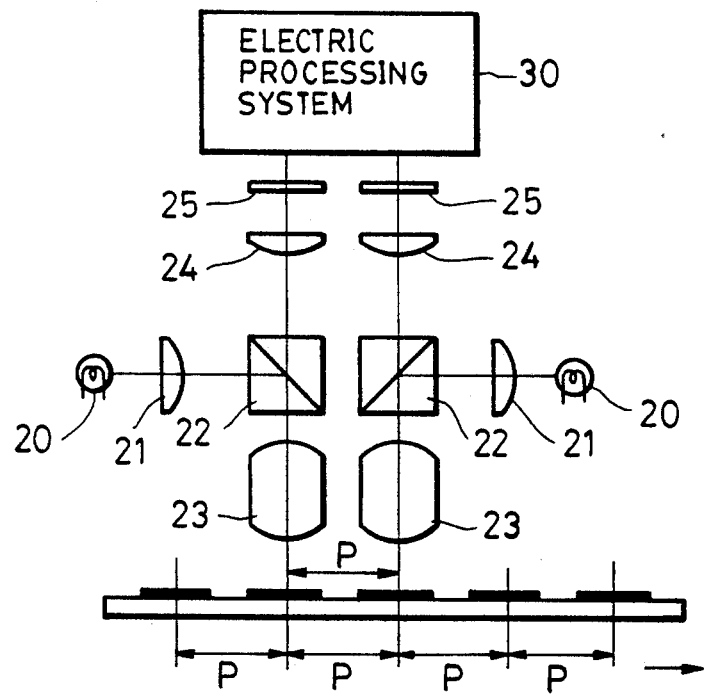
FIG. 8 illustrates the configuration of a third embodiment of the present invention.
Figure 9:
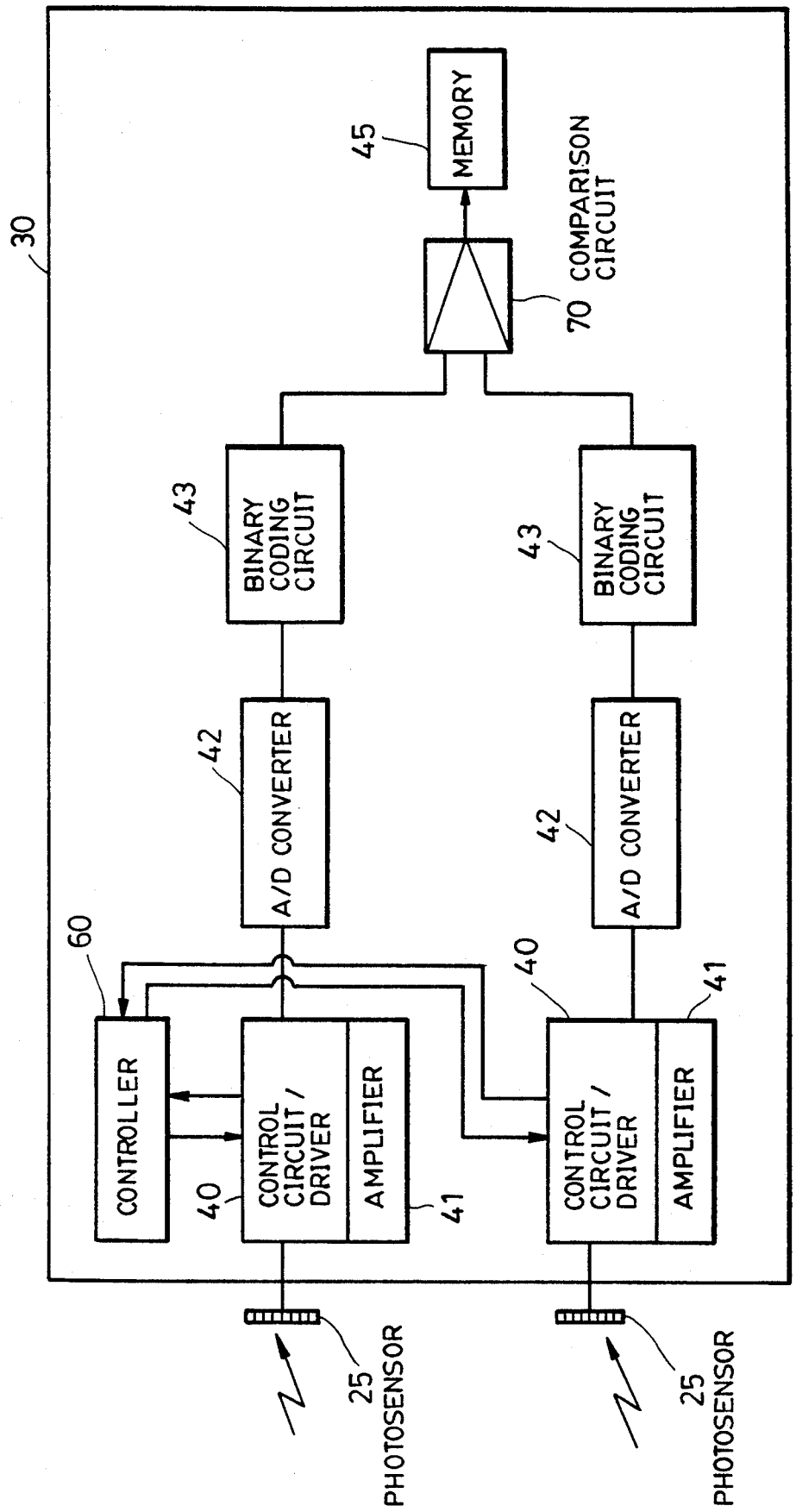
FIG. 9 is the circuit diagram of an electric processing system shown in the FIG. 8 embodiment.

FIG. 8 shows the configuration of a third embodiment of the present invention. This embodiment differs from the FIG. 3 embodiment in that two sets of optical systems for inspection are provided in parallel within a latent-image inspection unit. The distance between the optical axes of two objective lenses 23 is equal to the amount of a pitch (p) between adjacent chips when a reticle pattern is transferred to a wafer a plurality of times. The configuration of an electric processing system 30 is different from that shown in FIG. 4. That is, the same processing units are provided in place of the design data memory 47. It is unnecessary to read design data, but only output from two photosensors are processed in the same manner, and two resultant outputs are compared with each other by a comparison circuit 70 (FIG. 9).

Such a method is very effective when a plurality of chips (assumed to be three chips in the following explanation) are arranged on one reticle. The advantages of the method will be hereinafter described.

Figure 10:
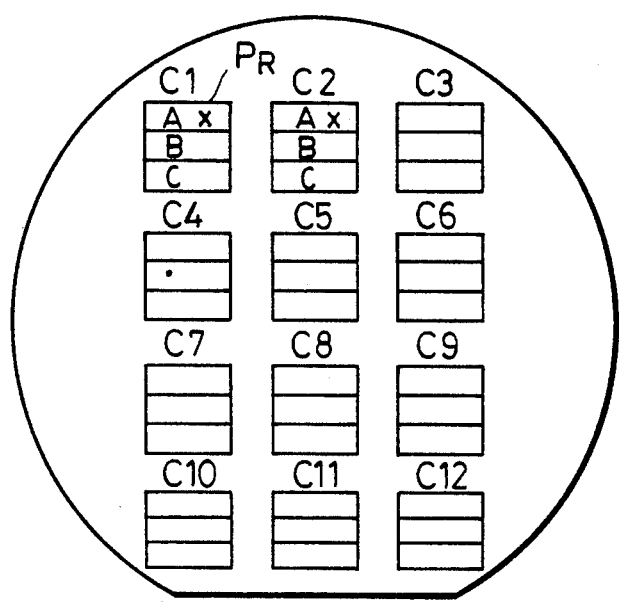
FIG. 10 illustrates an inspection method of the FIG. 8 embodiment.

FIG. 10 shows a state wherein a reticle pattern is repeatedly transferred to a wafer twelve times (12 chips C1–C12). Three identical pattern regions (A, B and C) are present on each chip.

First, one of the two objective lenses for inspection is set to region A on chip C1, and the other is set to region B on chip C2. Corresponding positions of the two regions are sequentially compared with each other. If two outputs differ from each other, the position ($P_R$) is stored in a memory.

Subsequently, the wafer is moved, and point $P_R$ within region C on chip C2 is inspected by any one of the objective lenses. The point to be inspected may be point $P_R$ within region C on chip C1. If the outputs from points $P_R$ in the above-described three regions are compared with one another, the output from one point is different from the outputs from the other two points. The point is assumed, for example, to be point $P_R$ within region A. Finally, point $P_R$ within region A on chip C2 is inspected. If it has the same output as point $P_R$ (the abnormal point) on chip C1, it is confirmed that point $P_R$ within region A represents a foreign particle on the reticle repeatedly transferred to all the chips.

On the contrary, if the output from point $P_R$ within region A on chip C2 is different from that (the abnormal point) on chip C1, it is considered that only point $P_R$ within region A on chip C1 is abnormal. In this case, it is determined that a foreign particle adhered to only that position on the wafer.

By performing the above-described chip comparison, electric processing is largely simplified, and a time loss to read design data disappears. Hence, processing speed is increased.

Figure 11:
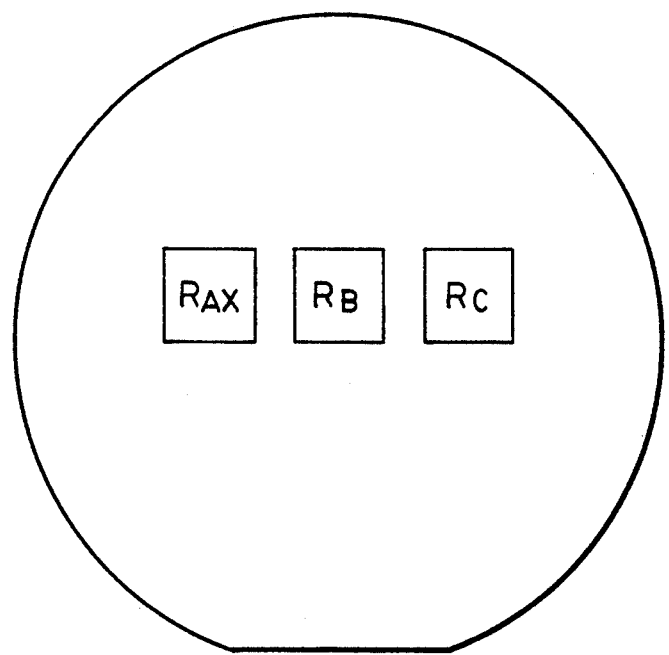
FIG. 11 illustrates another inspection method of the FIG. 8 embodiment.

FIG. 11 illustrates a case wherein the above-described inspection method is applied also to a 1 chip/1 reticle system. In this case, three reticles having an identical pattern are needed. The respective reticles are printed on one wafer for forming a latent image while being shifted (regions $R_A$, $R_B$ and $R_C$ in FIG. 11).

The three regions A, B and C in FIG. 10 correspond to the regions $R_A$, $R_B$ and $R_C$ in this case. Respective pair of these regions are inspected by the two objective lenses and compared with each other in the same manner as described above.

Figure 12:
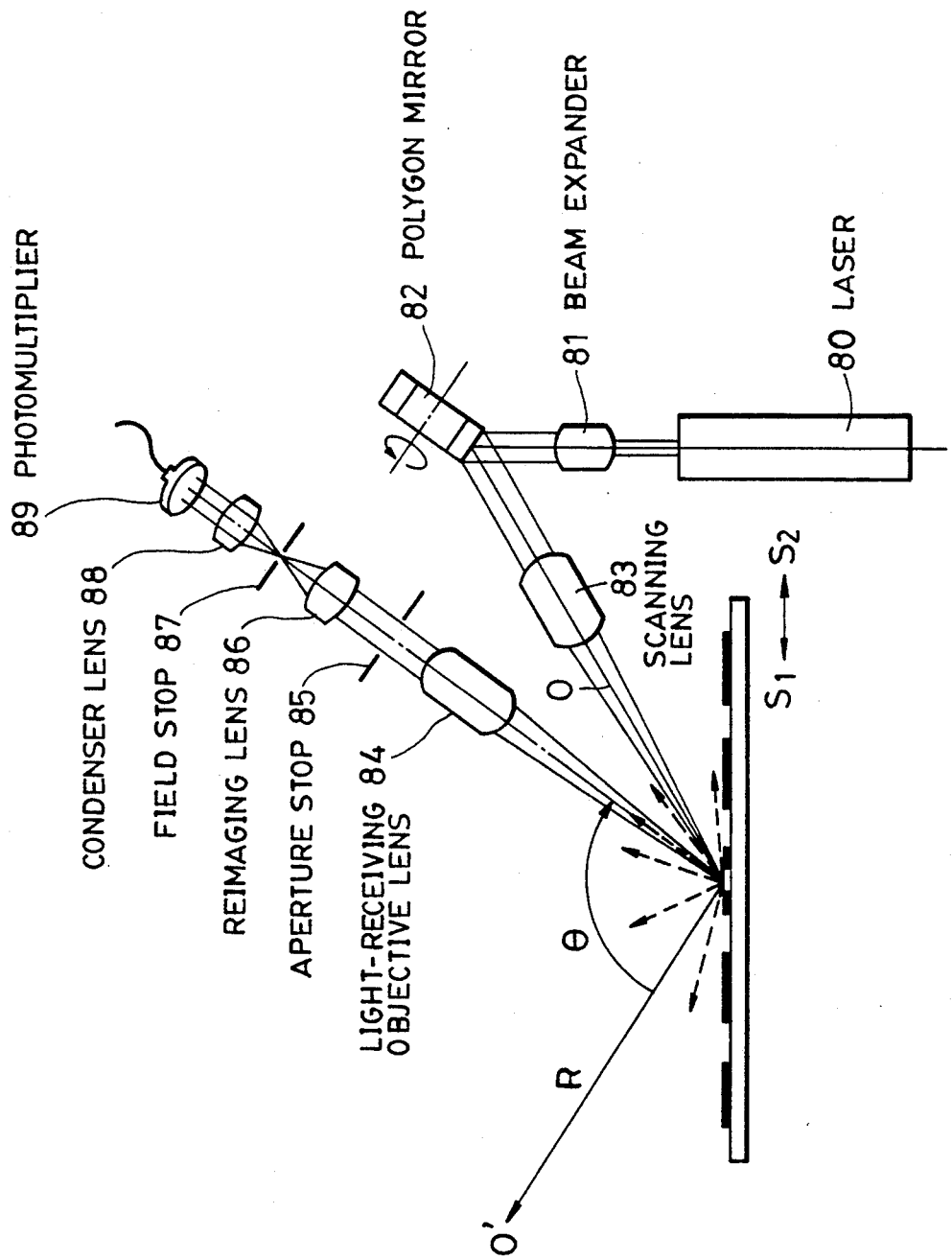
FIG. 12 illustrates the configuration of a fourth embodiment of the present invention.

FIG. 12 shows a fourth embodiment of the present invention. This embodiment differs from the FIG. 3 embodiment in that a different inspection method is used within the latent-image inspection unit. That is, a laser beam is obliquely incident upon a wafer, the beam is scanned in one direction (the direction perpendicular to the plane of FIG. 12), and light scattered by a foreign particle is detected. The wafer is moved in a direction $S_1 \longleftrightarrow S_2$) nearly perpendicular to the beam scanning direction in synchronization with the beam scanning to completely inspect the entire region to be inspected.

A beam issued from a laser 80 is expanded by a beam expander 81, and is incident upon a polygon mirror 82, which rotates within a surface perpendicular to the plane of FIG. 12. The beam focused on the wafer by a scanning lens 83 thereby scans in the direction perpendicular to the plane of FIG. 12.

A light-receiving optical system is set so as to aim at a beam scanning line formed on the wafer and so as not to receive light directly reflected from the wafer (to receive back-scattered light in FIG. 12). Scattered light from a foreign particle on the wafer spreads in almost all directions. The light beam in the scattered light captured by a light-receiving objective lens 84 assumes a parallel light beam after passing through it. At the position of the exit pupil of the light-receiving objective lens 84 is provided an aperture stop 85, which determines the diameter of a light beam to be captured. The scattered light beam passing through the stop 85 is refocused by a reimaging lens 86, and a position which is optically conjugate with the beam scanning line on the wafer is provided on the focused position. At this position is provided a (slitlike) field stop 87, which cuts extra flare light and the like except light from the scanning line. The scattered light beam diverges after passing through the field stop 87. The diverging light beam is paralleled by a condenser lens 88, and is received by a photomultiplier 89. The output from the photomultiplier 89 is output as foreign-particle information together with scanning-position information obtained, for example, from the revolution-angle information of the polygon mirror 82 and $S_1 \longleftrightarrow S_2$-direction movement information of the wafer.

By having the above-described arrangement, that is, the configuration wherein the beam is obliquely incident and the back-scattered light is detected, it is possible to increase the S/N ratio between the light (S) from a foreign particle and the light (N) from a circuit pattern. The reason is as follows: Diffracted light from the circuit pattern is generated accompanying the directly reflected light (R) from the upper surface of the wafer. The intensity of the diffracted light is reduced as its angle is separated from the directly reflected light (as angle $\theta$ shown in FIG. 12 increases). If the arrangement shown in FIG. 12 is adopted, a large angle $\theta$ can be provided. Hence, it is possible to increase accuracy in discriminating a foreign particle from a circuit pattern.

Figure 13:
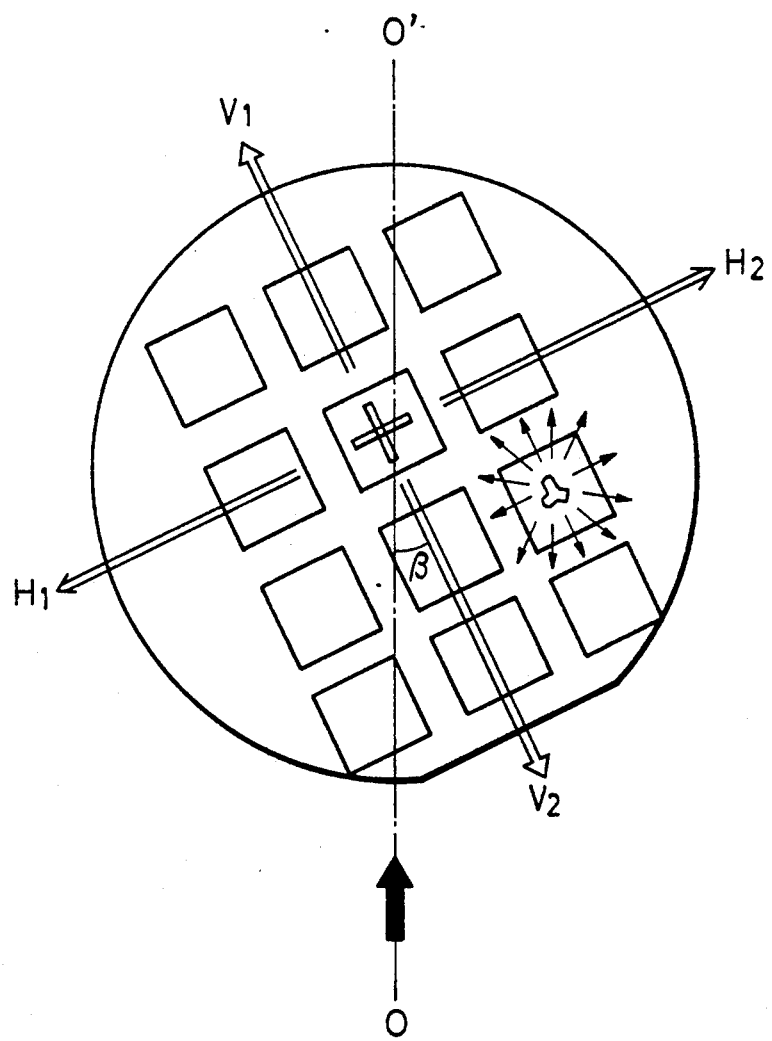
FIG. 13 illustrates a modified example of the fourth embodiment of the present invention.

FIG. 13 illustrates a configuration for increasing the S/N ratio between a foreign particle and a pattern. The configuration of the beam irradiation system and the light receiving system shown in FIG. 12 may be used. In this configuration, the projection line on the wafer of the optical axis of the optical system for inspection is twisted about 15° ($\beta°$) relative to the vertical and horizontal directions (directions $V_1V_2$ and $H_1H_2$ in FIG. 13) of the pattern on the wafer.

As described with reference to FIG. 6, diffracted light from the circuit pattern on the wafer is distributed in the directions perpendicular to the pattern. The direction of a line in a circuit pattern is most frequently in the vertical or horizontal direction, next frequently in ±45° directions, and in some cases in ±30+ and ±60+ directions. Accordingly, if the beam is incident while twisting the wafer by 15° relative to the optical system, and the light from the wafer is received within the plane of incidence, the diffracted light from the circuit pattern can be avoided. Since scattered light from a foreign particle is spread in all directions, the detection rate of foreign particles is greatly increased if the scattered light is captured in the plane of incidence.

Next, an explanation will be provided of an embodiment which comprises exposure/transfer means for exposing and transferring a pattern of an original to a plurality of shot positions on a substrate using a projection optical system, and inspection means for inspecting a negative image composed of a photochromic image of the pattern of the original formed on the substrate by the exposure/transfer means to detect the presence of a foreign particle on the original.

The exposure/transfer means includes, for example, an excimer laser as a light source for illumination.

The detection means includes, for example, a memory storing the data of the pattern of the original, and compares the data with the photochromic image of the pattern of the original formed on the substrate.

The detection means includes, for example, a spatial filter.

When using an original having a plurality of identical patterns, the detection means includes, for example, two-channel image detection means for simultaneously detecting image data of an identical pattern portion within one shot and between different shots of photochromic images for at least two shots of the patterns formed on the same substrate, and comparison means for comparing the image data of the identical pattern portion detected by the detection means with one another.

Alternatively, even when not using the above-described original, the detection means includes, for example, at least two-channel image detection means for simultaneously detecting image data of at least two identical pattern portions in respective photochromic images formed on the same substrate using at least three originals having an identical pattern, and comparison means for comparing the image data of the identical pattern portions detected by the detection means.

The detection means further includes, for example, means for scanning laser light while obliquely irradiating it relative to the photochromic images, and for receiving scattered light issued from the photochromic images at that time to detect image data of the photochromic images, and phase difference detection means.

In the above-described configuration, before actually printing product wafers, a substrate coated with a resist on which negative images composed of photochromic images are formed is used in order to inspect the presence of dust on the original. The pattern of the original is printed on the resist by the exposure/transfer means. The photochromic images of the pattern of the original printed on the resist are detected by the detection means, and the presence of a foreign particle of a level influencing printing on the original is detected. Due to the characteristic of the negative image, only dust adhered to transparent portions on the original is detected.

The present embodiment will now be explained with reference to the drawings.

Figure 14:
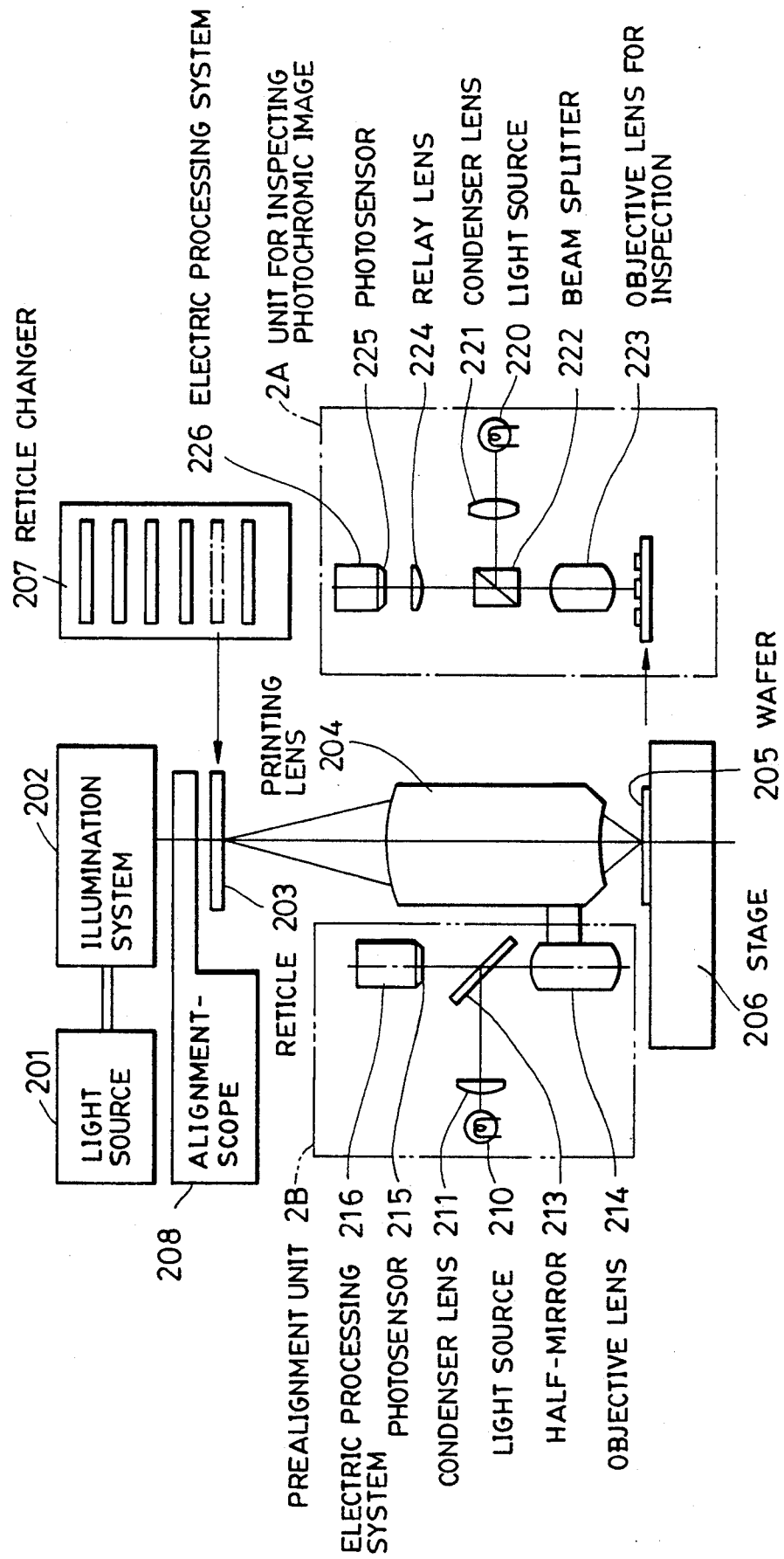
FIG. 14 is a schematic diagram showing an exposure apparatus according to a fifth embodiment of the present invention.

FIG. 14 shows an exposure apparatus according to a fifth embodiment of the present invention. In FIG. 14, a light source 201 for printing comprises an extra-high-pressure mercury-vapor lamp, an excimer laser or the like. An illumination system 202 uniformly irradiates a light beam emitted from the light source 201 with a predetermined aperture angle. The entire surface of a reticle 203 is illuminated by the illumination system 202. There are also shown a printing lens 204 and a reticle changer 207. The reticle 203 is fed from the reticle changer 207 to the object surface (an exposure stage 206) of the printing lens 204. A circuit pattern on the reticle 203 is subjected to reduced transfer to a wafer 205 by the printing lens 204. The wafer 205 is coated with a layer (a photochromic material) on which photochromic images are to be formed. The photochromic material is a material to cause photochromism wherein its absorption spectra is reversibly changed by light irradiation, and is represented by a spiropyran-type material or the like. There is also shown a unit 2A for inspecting the photochromic images. In the present embodiment, after transferring at least one shot of the reticle pattern to the wafer 205, the wafer 205 is moved to the stage 206, and is fed to the inspection unit 2A for inspection.

The inspection unit 2A includes a light source (either a laser or a halogen lamp with a color filter may be used) 220 for inspection which emits a light beam having a wavelength within a wavelength range wherein the photochromic image on the wafer 205 can be observed and the image is not erased. The light beam illuminates an image forming region (a transfer region of the reticle pattern) on the wafer 205 via a condenser lens 221, a beam splitter 222 and an objective lens 223 for inspection. The light reflected from the wafer 205 is incident upon a relay lens 224 via the objective lens 223 for inspection and the beam splitter 222, and is condensed on a photosensor 225 by the function of the relay lens 224. The surface of the wafer 205 and the photosensitive surface of the photosensor 225 are optically conjugate with each other. The photosensor 225 comprises a light-position sensor, such as a two-dimensional CCD array or a pickup tube. The circuit pattern on the reticle including foreign particles is first transferred to the wafer, and is then imaged on the photosensitive surface of the photosensor 225. The output from the photosensor 225 is processed by an electric processing system 226 to detect foreign particles.

Figure 15:
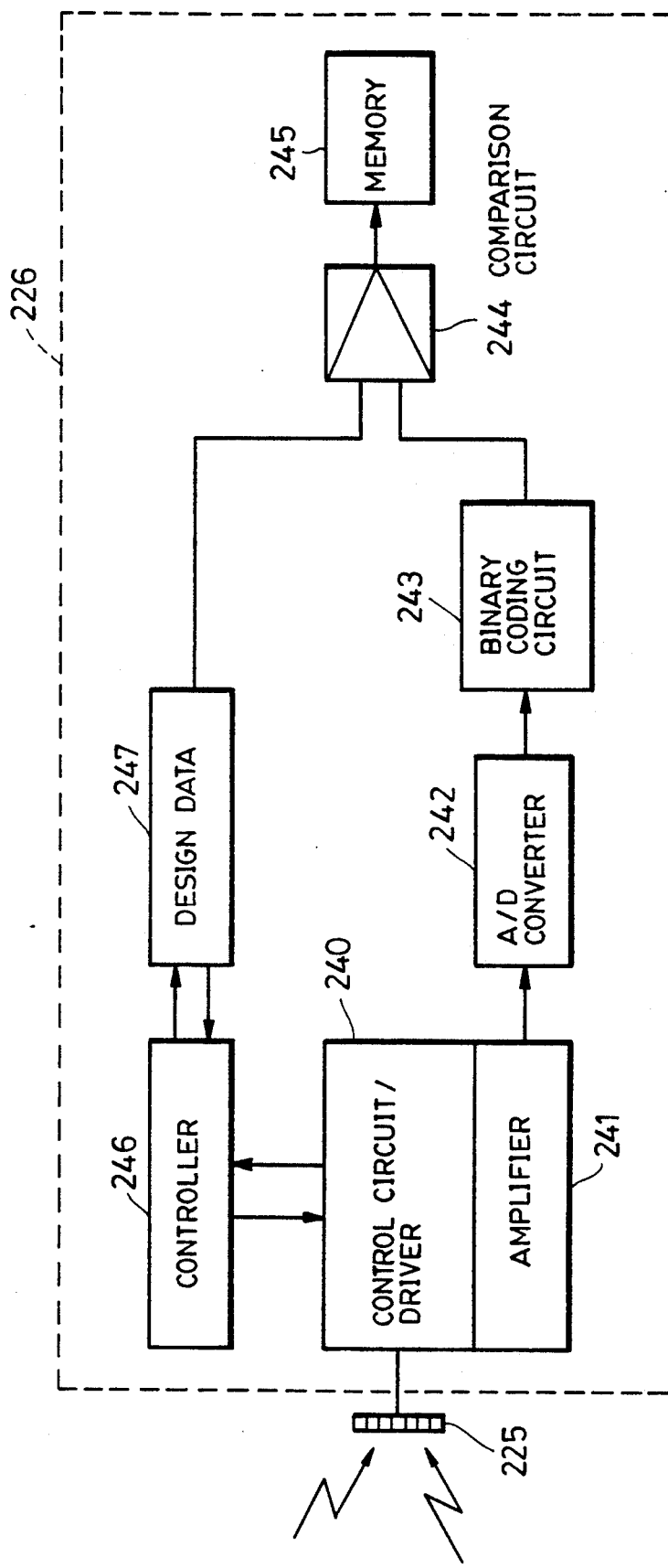
FIG. 15 is a block diagram showing an electric processing system of the FIG. 14 apparatus.

FIG. 15 is a block diagram showing the configuration of the electric processing system 226. An output from the light-position sensor 225 is received in a control circuit/driver 240 whose timing is controlled by a controller 246 which commands the setting of inspection conditions, for example, the start and end of positioning inspection of the wafer 205. The received signal is amplified by an amplifier 241. The amplified signal is digitized by an A/D converter 242, is then subjected to binary coding by a binary coding circuit 243, and is output to a comparison circuit 244. The controller 246 reads design data of the reticle pattern previously stored in a memory 247, and outputs the data to the comparison circuit 244. The comparison circuit 244 compares the output from the memory 247 with the output from the binary coding circuit 243. If the two output data do not coincide with each other, the controller 246 determines that a foreign particle is present, and stores its position, size and the like within the memory 245.

A negative image, such as a photochromic image, has the characteristic that a light absorber is formed in portions irradiated by light, and the light-and-dark state of the reticle pattern is therefore reversed. Accordingly, even by inspecting only one chip on the wafer, a foreign particle adhered to the reticle can be discriminated from a foreign particle adhered to the wafer in the following way:

FIG. 16(A) is a horizontal cross-sectional view of a reticle subjected to patterning. A foreign particle $P_R$ adheres to the reticle. FIG. 16(D) shows a design data $S_A$ relative to the reticle output from the memory 247. FIG. 16(B) shows the state of a wafer coated with a resist for forming photochromic images before exposure. If the wafer is inspected in this state, the entire output from a binary coding circuit 248 assumes a high level, because a resist of this kind is transparent and the reflectivity of the wafer substrate is high. If a reticle pattern is transferred to the resist, exposed portions 251 absorb inspection light due to a chemical reaction. Portion $P_R'$ corresponding to the foreign particle $P_R$ adhered to the reticle remains transparent. On the contrary, a foreign particle $P_W$ adhered to the wafer after light exposure prevents a light beam for inspection from irradiating the wager substrate. As a result, the output from the binary coding circuit 248 corresponding to this portion assumes a low level. Accordingly, the output $S_C$ from the binary coding circuit 248 when the wafer in the state shown in FIG. 16(C) is inspected becomes as shown in FIG. 16(E). If the logical sum of an inverted output of the output $S_C$ and the output $S_A$ from the memory 247 is provided, and its inverted value $\overline{(S_A \oplus S_C)}$ is finally output, it is possible to determine by inspection that the detected substance is a foreign particle adhered to the reticle.

In FIG. 16(C), the foreign particle $P_W$ adhered to the wafer is situated on an unexposed portion of the wafer. If it is situated on an exposed portion, the output $S_C$ assumes a low level from the above-described characteristic of the negative image. Hence, the result of inspection is not influenced by the presence of the particle $P_W$.

Referring again to FIG. 14, an alignment unit 2B positions the wafer 205. After being aligned, the wafer 205 is positioned at an exposure position by being moved a predetermined amount. As described above, there are two methods in gross for finally positioning a wafer relative to a reticle, that is, the TTL method wherein an alignment-scope 208 is used, and the off-axis method wherein the alignment-scope 208 is not used. The unit 2B functions differently in each method.

Anyway, the basic configuration of the unit 2B consists of a light source 210, an objective lens 214, a photosensor 215 and an electric processing system 216. The light source 210 illuminates a predetermined mark on the wafer via a condenser lens 211, a half-mirror 213 and an objective lens 214. The image of the mark included in the reflected light is imaged onto the photosensor 215 of the electric processing system 216 by the objective lens 214. By performing photoelectric conversion of the image and processing a signal as a result of the conversion, the position of the wafer is detected. The wafer is moved according to the result of detection to perform alignment. Accordingly, in consideration of the configuration of the entire stepper apparatus, the alignment unit 2b may have the function of the unit 2A for inspecting photochromic images. That is, the configuration of the electric processing system 226 shown in FIG. 15 may be added to the electric processing system 216, and the wafer may be returned to the unit 2B when inspecting photochromic images to perform the above-described image inspection.

By adopting the above-described configuration, the following effects may be obtained:

(1) Since inspection is performed by actually setting a substrate, such as a reticle or the like, at an exposure position and by printing a pattern of the substrate on a wafer, (a) overlooking a foreign particle due to its shape which might occur in the conventional laser scanning method will never occur, (b) and overlooking due to a difference in wavelength between exposure light and inspection light which might occur in the conventional laser scanning method will never occur.

(c) Furthermore, since an inspection equivalent to the inspection at the exposure position is performed, a reticle is not influenced by dust within the apparatus while the reticle is carried to the exposure position after having been inspected at a reticle changer portion as in the prior art.

(d) Moreover, since inspection is performed through a printing lens, only foreign particles influencing a product wafer including the performance of the actual printing lens can be detected.

(2) Since it is unnecessary to take a printed wafer out of the apparatus to develop it, the entire inspection time can be greatly decreased. Furthermore, misdetection caused by inferior pattern edges due to etching processing and the like will never occur.

(3) Since the region to be inspected on a wafer is reduced to about 1/5 (depending on the reduction ratio of the printing lens) of the region when a reticle is directly inspected, it is possible to provide a compact inspection unit.

Figure 17:
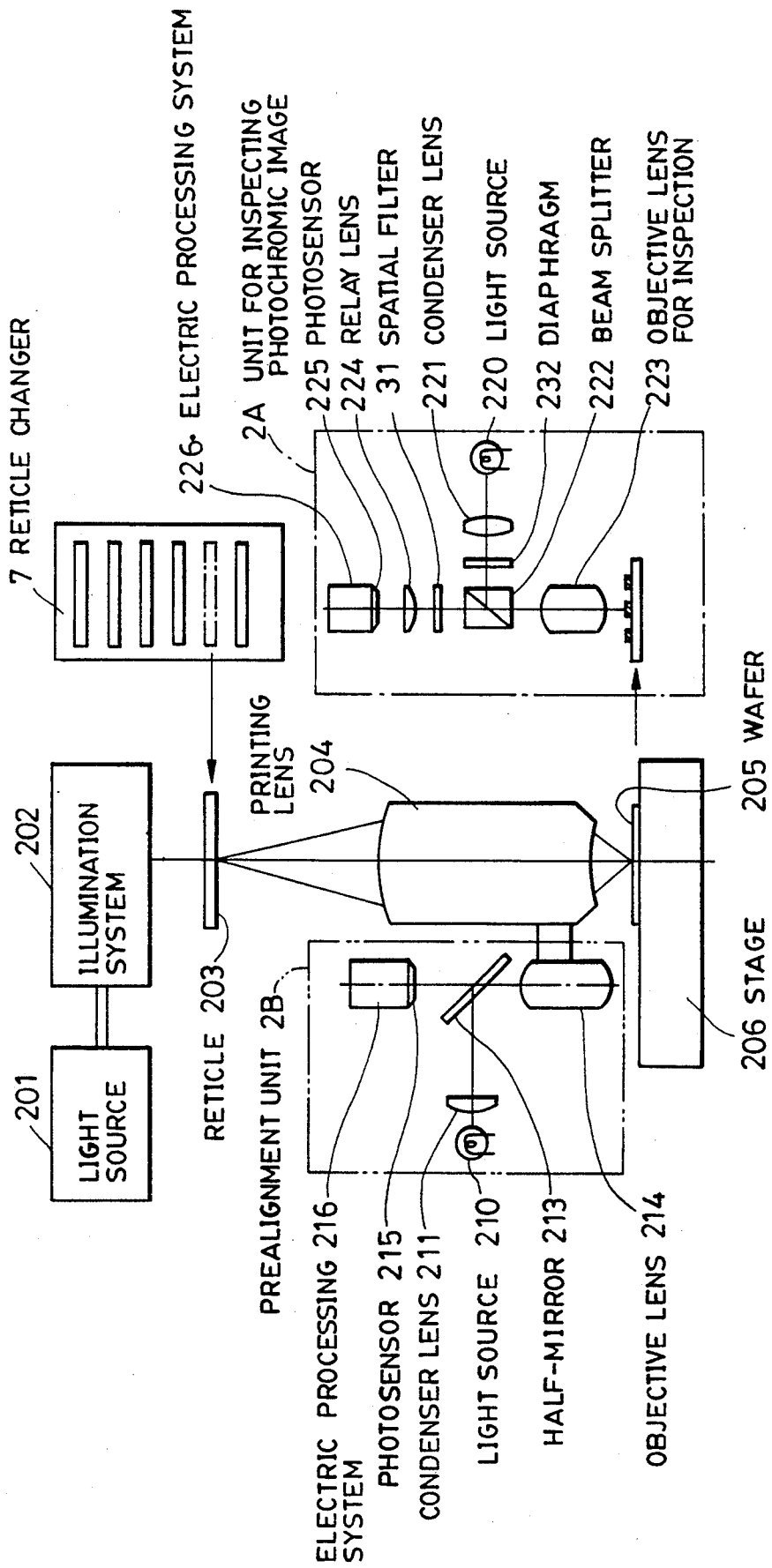
FIG. 17 is a schematic diagram showing an exposure apparatus according to a sixth embodiment of the present invention.

FIG. 17 above a sixth embodiment of the present invention. This embodiment differs from the fifth embodiment in that the spatial filter 31 is used between the beam splitter 222 and the relay lens 224 of the inspection unit 2A. The advantages when the spatial filter 31 is inserted are the same as those explained with reference to FIG. 6, though photochromic images are used in the present embodiment.

According to the function of the spatial filter 31, only foreign particles can be electrically detected in a state wherein circuit patterns (photochromic images) on a wafer are cancelled. In this case, as in the case of the second embodiment, since comparison of the obtained data with the design data stored in the memory 247 shown in FIG. 15 becomes unnecessary, the configuration of the electric system 226 is largely simplified.

Also in the present embodiment, as in the detection in the second embodiment, the spatial filter 31 and the diaphragm 32 shown in FIGS. 7(a)-7(d) may be used.

Figure 18:
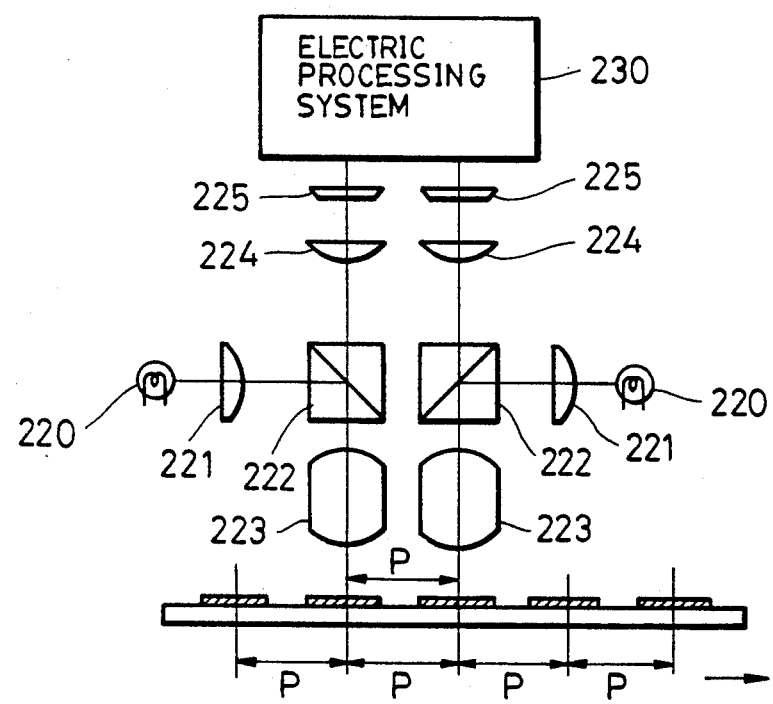
FIG. 18 is a schematic diagram showing a unit for inspecting photochromic images according to a seventh embodiment of the present invention.
Figure 19:
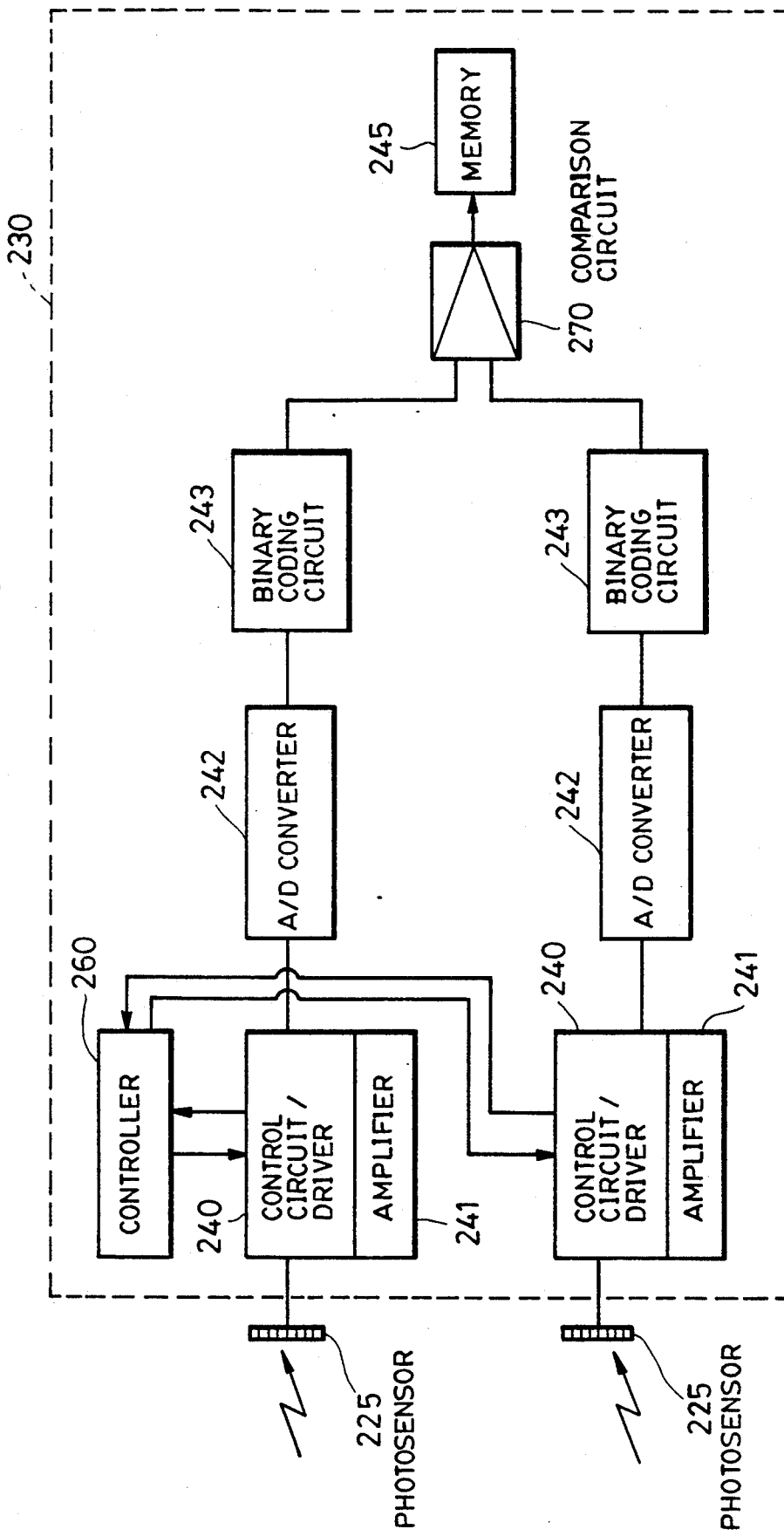
FIG. 19 is a block diagram showing an electric processing system of the FIG. 18 apparatus.

FIG. 18 shows a unit for inspecting photochromic images according to a seventh embodiment of the present invention. The present embodiment differs from the fifth embodiment in that two sets of optical systems for inspection each composed of the light source 220 through the photosensor 225 of the photochromic-image inspection unit 2A are provided in parallel. The distance between the optical axes of the two objective lenses 223 is equal to the amount of pitch P between adjacent chips when a reticle pattern is transferred to a wafer a plurality of times. The configuration of an electric processing system 230 is different from the configuration shown in FIG. 15. As shown in FIG. 19, it is unnecessary to read design data, but only outputs from the two photosensors are compared with each other by a comparison circuit 270 via control circuit/drivers 240 through binary-coding circuits 243 by the control of a controller 260.

Such a method is very effective when a plurality of chips (assumed to be three chips in the following explanation) are arranged on one reticle (that is, three chips/one reticle). The advantages of the method will be hereinafter described.

Figure 20:
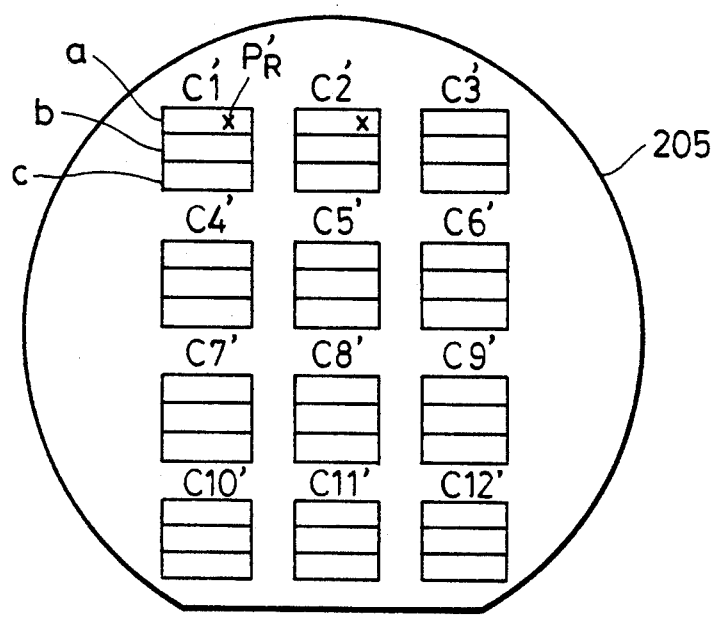
FIG. 20 illustrates an inspection procedure using the FIG. 18 apparatus in the case of 3 chips/1 reticle.

FIG. 20 shows a state wherein a reticle pattern is repeatedly transferred to the wafer 205 twelve times (for 12 chips C1'-C12'). Three identical pattern regions a-c are present within each chip.

First, one of the two objective lenses 223 for inspection is set to region "a" on chip C1', and the other is set to region "b" on chip C2'. Corresponding positions of the two regions are sequentially compared with each other. If two outputs differ from each other, the position $P_R'$ is stored in a memory 245.

Subsequently, the wafer is moved, and point $P_R'$ within region "c" on chip C2' is inspected by any one of the objective lenses 223. The point to be inspected may be point $P_R'$ within region "c" on chip C1'. If outputs from points $P_R'$ in the above-described three regions are compared with one another, the output from one point $P_R'$ in region "a" is different from the outputs from the other two points. Finally, point $P_R'$ within region "a" on chip C2 is inspected. If it has the same output as point $P_R'$ (the abnormal point) on chip C1', it is confirmed that point $P_R'$ within region "a" represents a foreign particle on the reticle repeatedly transferred to all the chips. On the contrary, if the output from point $P_R'$ within region "a" on chip C2' is different from that (the abnormal point) on chip C1', it is considered that only point $P_R'$ within region "a" on chip C1' is abnormal. In this case, it is determined that a foreign particle, for example, adhered to only that position on the wafer.

By performing the above-described chip comparison, processing in the electric processing system is largely simplified, and a time loss to read design data disappears. Hence, processing speed is increased.

Figure 21:
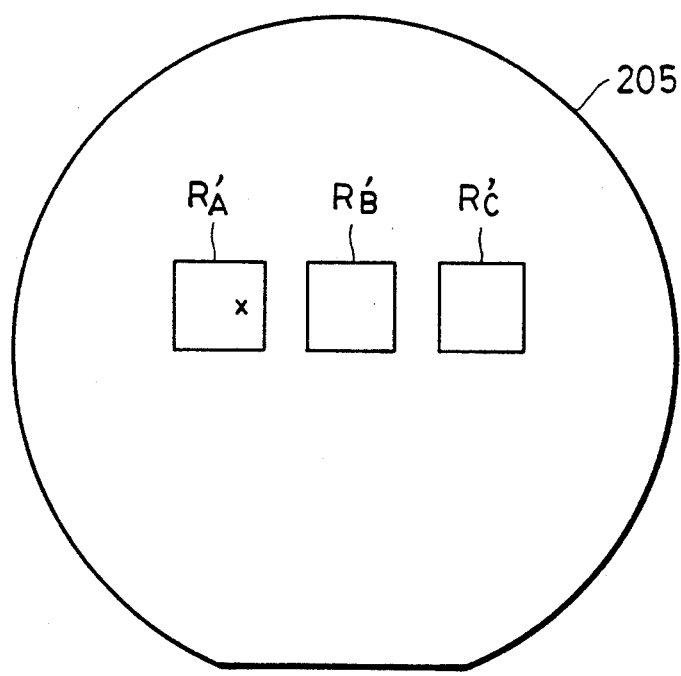
FIG. 21 illustrates an inspection procedure using the FIG. 18 apparatus in the case of 1 chip/1 reticle.

FIG. 21 illustrates a case wherein the above-described inspection method is applied also to a 1 chip/1 reticle system. In this case, three reticles having an identical pattern are needed. Images $R_A'$-$R_C'$ obtained from the respective reticles are printed on one wafer for forming photochromic images while being shifted.

The three regions "a", "b" and "c" in FIG. 20 correspond to the regions $R_A'$-$R_C'$ in this case. Respective pair of these regions are inspected by the two objective lenses and compared with each other as in the above-described manner.

Figure 22:
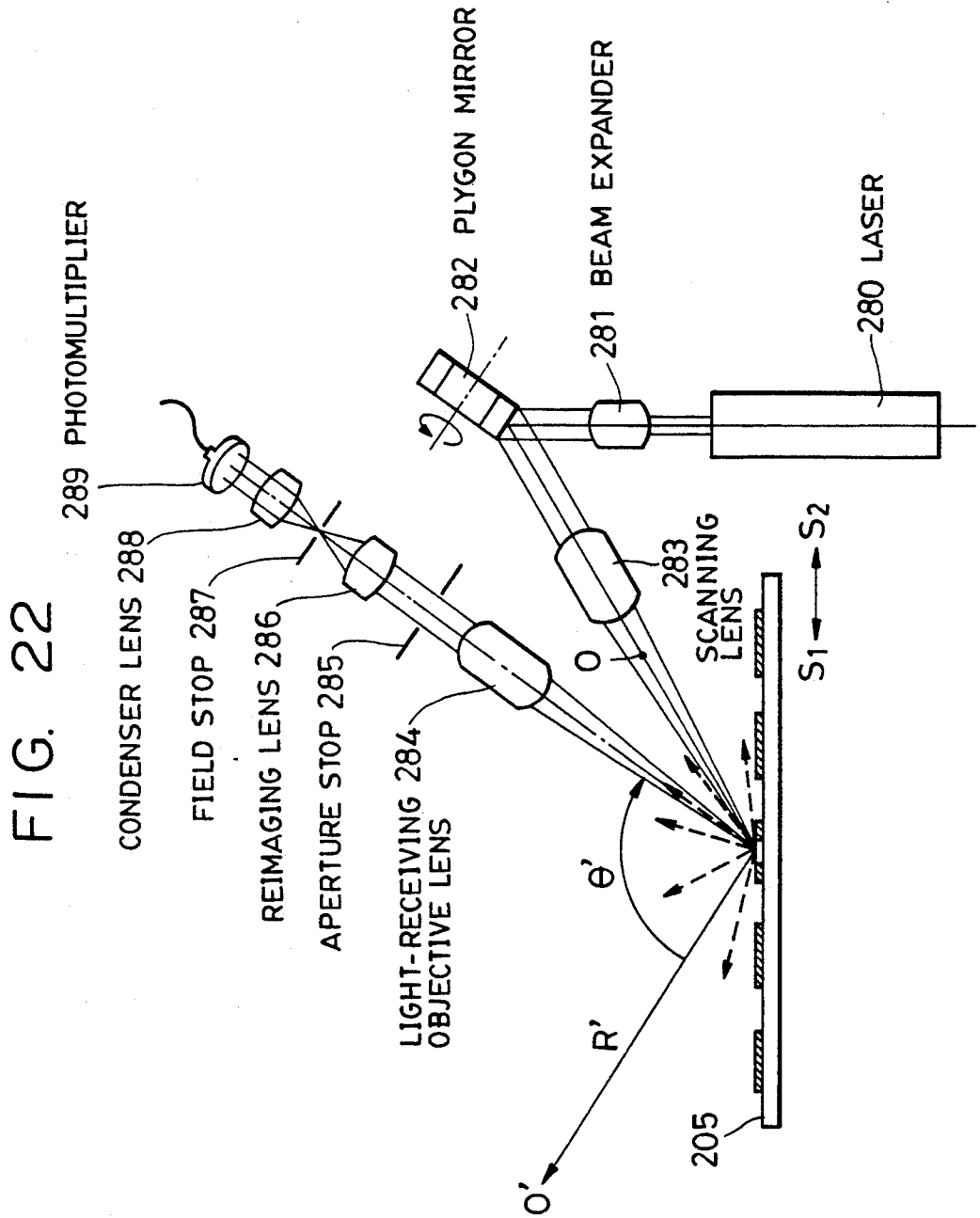
FIG. 22 is a schematic diagram showing a unit for inspecting photochromic images according to an eighth embodiment of the present invention.

FIG. 22 shows a unit for inspecting photochromic images according to an eighth embodiment of the present invention. The inspection method in this embodiment differs from that in the fifth embodiment. That is, a laser beam is obliquely incident upon the wafer 205, the beam is scanned in one direction (the direction perpendicular to the plane of FIG. 22), and light scattered by a foreign particle is detected. The wafer 205 is moved in direction $S_1$ and $S_2$ nearly perpendicular to the beam scanning direction in synchronization with the beam scanning to completely inspect the entire region to be inspected.

That is, a beam issued from a laser 280 is expanded by a beam expander 281, and is incident upon a polygon mirror 282, which rotates within a surface perpendicular to the plane of FIG. 22. The beam focused on the wafer 205 by a scanning lens 283 thereby scans in the direction perpendicular to the plane of FIG. 22. A light-receiving optical system is set so as to aim at a beam scanning line formed on the wafer 205, and the optical axis of the system is set so as not to receive light directly reflected from the wafer 205. The optical axis of the system is set, for example, so as to receive back-scattered light in the case of FIG. 22. Scattered light from a foreign particle on the wafer 205 spreads in almost all directions. The light beam in the scattered light captured by a light-receiving objective lens 284 becomes a parallel light beam after passing through it. An aperture stop 285 provided at exit of the light-receiving objective lens 284 determines the diameter of a light beam to be captured. The scattered light beam passing through the aperture stop 285 is refocused by a reimaging lens 286, and a position which is optically conjugate to the beam scanning line on the wafer 205 is provided on the focused position. At this position is provided a slitlike field stop 287, which cuts extra flare light and the like except light from the scanning line. The scattered light beam diverges after passing through the field stop 287. The diverging light beam is paralleled by a condenser lens 288, and is received by a photomultiplier 289. The output from the photomultiplier 289 is output as foreign-particle information together with, for example, scanning-position information.

As described above, by detecting the back-scattered light of an obliquely incident laser beam, it is possible to increase the S/N ratio between the light (S) from a foreign particle and the light (N) from a circuit pattern. The reason is as follows: Diffracted light from the circuit pattern is generated accompanying the directly reflected light R' from the upper surface of the wafer 205. The intensity of the diffracted light is reduced as its angle is separated from the directly reflected light, that is, as angle $\theta'$ shown in FIG. 22 increases. If the arrangement shown in FIG. 22 is adopted, a large angle $\theta'$ can be provided. Hence, it is possible to increase accuracy in discriminating a foreign particle from a circuit pattern.

Figure 23:
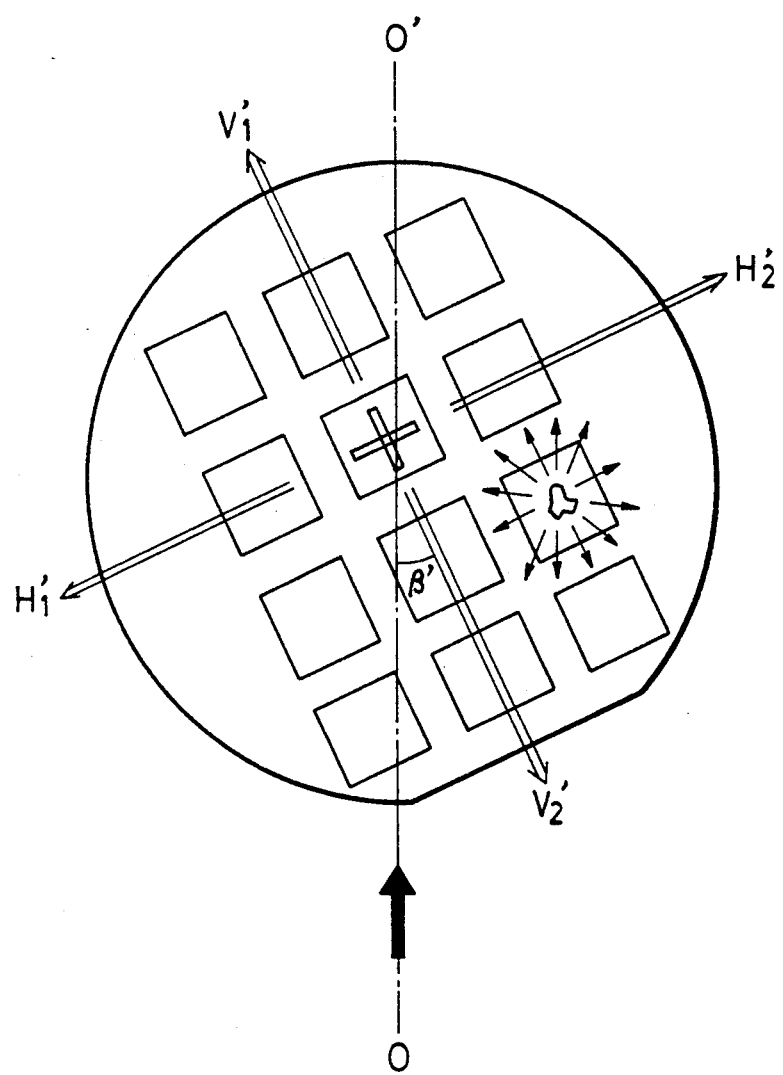
FIG. 23 illustrates an improved method of the eighth embodiment of the present invention.

FIG. 23 illustrates a method for increasing the S/N ratio between a foreign particle and a pattern.

The beam irradiation system and the light receiving system shown in FIG. 22 may be used. It is only necessary that the projection line on a wafer of the optical axis of the optical system for inspection has an angle of about $\beta = 15°$ relative to the vertical and horizontal directions (directions $V_1'V_2'$ and $H_1'H_2'$ in FIG. 23) of the pattern, as shown in FIG. 23.

As described with reference to FIG. 6, diffracted light from the circuit pattern on the wafer is distributed in the direction perpendicular to the pattern. The direction of a line in a circuit pattern is most frequently in the vertical or horizontal direction, next frequently in $\pm 45°$ directions, and in rare cases in $\pm 30°$ and $\pm 60°$ directions. Accordingly, if the beam is incident while twisting the wafer 15° relative to the optical system, and the light from the wafer is received within the plane of incidence, the diffracted light from the circuit pattern can be avoided. Since scattered light from a foreign particle is spread in all directions, the detection rate of foreign particles is greatly increased if the scattered light is captured in the plane of incidence.

In the foregoing fifth through eight embodiments, since foreign particles on an original are inspected by inspecting negative images of the pattern of the original formed on a substrate in an undeveloped state, foreign particles will not adhere to the substrate in the following processes, such as development and the like. Furthermore, even if a foreign particle adheres to the substrate before foreign-particle inspection, the particle can be discriminated from foreign particles on the original according to a difference in light and darkness. The negative images are not limited to photochromic images, but may also be images formed on a resist to be developed before development, that is, latent images. In this case, a negative-type resist is used.

The present invention may be applied not only to a reduction-type projection exposure apparatus (a stepper), but also, for example, to a unit-magnification-type exposure apparatus making, for example, a printing lens, as shown, for example, in FIG. 3, a unit-magnification mirror projection system, and a proximity-type exposure apparatus wherein printing is performed while making an original and a wafer in close contact with each other without using the printing lens 4 shown, for example, in FIG. 3.

Furthermore, the present invention may be applied not only to light exposure, but also to X-ray exposure and the like.

In the above-described printing for inspection, a printing apparatus, such as a stepper or the like, actually used for wafer printing is not necessarily used, but a printing apparatus for performing printing for inspection may be separately provided.

Furthermore, the formation of latent images and the formation of photochromic images are not necessarily performed using light having a wavelength identical to that of light for printing actually used, for example, in pattern printing on a wafer in the semiconductor production process.

For example, if the above-described printing for inspection is performed rather using light having a wavelength to which a resist for forming a latent image or a photochromic film is most sensitive within a practical range, that is, within a wavelength range wherein foreign particles, such as opaque dust particles and the like, causing a problem in the printing wavelength can be detected, the printing has the effect of shortening printing time. In the case of separately providing a printing apparatus for printing for inspection as described above, the advantage of shortening printing time can be fully utilized because an optical system and the like designed so as to be optimum for the wavelength of light for inspection may be mounted on the printing apparatus for inspection.

What is claimed is:

1. A method for inspecting a surface condition of an original having a pattern, comprising the steps of:
    illuminating the original;
    transferring images of the pattern on the original to a transfer member disposed at a position for pattern transfer; and
    inspecting the images transferred to the transfer member to determine the surface condition of the original, said image inspection being performed after said image transfer step without passing through developing processing.

2. A method according to claim 1, wherein the transfer member includes a photosensitive material, and wherein said inspecting step includes inspection of undeveloped images formed on the photosensitive material by the illumination of the original during said transferring step.

3. A method according to claim 1, wherein the transfer member includes a photochromic film, and wherein said inspecting step includes inspection of photochromic images formed on the photochromic film by the illumination of the original during said transferring step.

4. A method according to claim 1, wherein negative images of the pattern of the original are formed on the transfer member by said image transfer step.

5. A method according to claim 1, wherein said image inspection is performed by comparing the images with previously stored pattern information of the original.

6. A method according to claim 1, wherein said image inspection is performed by comparing a plurality of portions of the images corresponding to a plurality of identical pattern portions in patterns on one or a plurality of originals with one another.

7. A method according to claim 1, wherein said image inspection comprises the steps of illuminating light on the images, detecting light scattered from the images illuminated by the light, and inspecting image information obtained by said detection of the scattered light.

8. A method according to claim 1, wherein said illumination is performed using excimer laser light.

9. A method according to claim 1, wherein said illumination is performed using light from an extra-high-pressure mercury-vapor lamp.

10. A method according to claim 1, wherein said transfer is performed through a projection system.

11. An apparatus for inspecting a surface condition of an original having a pattern to be transferred using a transfer apparatus, said apparatus for inspecting comprising:
    image detection means for detecting undeveloped images of the pattern of the original formed on a photosensitive material on a transfer member by the transfer apparatus; and
    surface condition inspection means for inspecting the surface condition of the original according to image detection by said image detection means.

12. An apparatus for inspecting a surface condition of an original having a pattern to be transferred using a transfer apparatus, said apparatus for inspecting comprising:
    photochromic image detection means for detecting photochromic images of the pattern of the original formed on a transfer member having a photochromic film by said transfer apparatus; and
    surface condition inspection means for inspecting the surface condition of the original according to photochromic image detection by said photochromic image detection means.

13. A transfer apparatus for transferring a pattern on an original, comprising:
    exposure means for performing exposure in order to transfer the pattern of the original to a transfer member, undeveloped images of the pattern being capable of being formed by exposure by said exposure on a photosensitive material on the transfer member; and
    image inspection means for inspecting the undeveloped images formed on the photosensitive material, a surface condition of the original being inspected by image inspection by said image inspection means.

14. A transfer apparatus according to claim 13, further comprising a projection system for projecting the pattern of the original illuminated by said exposure means onto the photosensitive material on the transfer member.

15. A transfer apparatus according to claim 14, wherein said exposure means includes an excimer laser as a light source.

16. A transfer apparatus according to claim 13, wherein said image inspection means discrimination foreign particles on the original from foreign particles on the photosensitive material.

17. A transfer apparatus for transferring a pattern of an original, comprising:
    exposure means for performing exposure in order to transfer the pattern of the original to a transfer member, photochromic image of the pattern being capable of being formed on a photochromic film on a member having the photochromic film by exposure by said exposure means; and
    photochromic image inspection means for inspecting the photochromic images formed on the photochromic film, a surface condition of the original being inspected by photochromic image inspection by said photochromic image inspection means.

18. A transfer apparatus according to claim 17, further comprising a projection system for projecting the pattern of the original illuminated by said exposure means onto the transfer member.

19. A transfer apparatus according to claim 18, wherein said exposure means includes an excimer laser as a light source.

20. A transfer apparatus according to claim 17, wherein said photochromic image inspection means has a function to discriminate foreign particles on the original from foreign particles on the photochromic film.

21. An apparatus for inspecting a surface condition of an original having a pattern to be transferred using a transfer apparatus, said apparatus for inspecting comprising:
    a photosensor for detecting undeveloped images of the pattern of the original formed on a photosensitive material on a transfer member by the transfer apparatus, said photosensor generating output on the basis of detection of the undeveloped images; and a processing system for inspecting the surface condition of the original according to the output from said photosensor.

22. An apparatus according to claim 21, wherein said processing system processes the output from said photosensor to detect foreign particles on the original.

23. An apparatus for inspecting a surface condition of an original having a pattern to be transferred using a transfer apparatus, said apparatus for inspecting comprising:

a photosensor for detecting photochromic images of the pattern of the original formed on a transfer member having a photochromic film by the transfer apparatus, said photosensor generating output on the basis of detection of the photochromic images; and a processing system for inspecting the surface condition of the original according to the output from said photosensor.

24. An apparatus according to claim 23, wherein said processing system processes the output from said photosensor to detect foreign particles on the original.

* * * * *

UNITED STATES PATENT AND TRADEMARK OFFICE
CERTIFICATE OF CORRECTION

PATENT NO. : 5,162,867
DATED : November 10, 1992
INVENTOR(S) : MICHIO KOHNO

It is certified that error appears in the above-indentified patent and that said Letters Patent is hereby corrected as shown below:

SHEET 18 OF 19

"PLYGON" should read --POLYGON--.

COLUMN 4

Line 39, "alignmentscope" should read --alignment-scope--.

COLUMN 6

Line 42, "output" should read --outputs--.

COLUMN 16

Line 35, "discrimination" should read --discriminates--.

Signed and Sealed this

Twenty-fifth Day of January, 1994

Attest:

BRUCE LEHMAN

*Attesting Officer*    *Commissioner of Patents and Trademarks*